United States Patent
Osumi

(10) Patent No.: US 9,113,826 B2
(45) Date of Patent: Aug. 25, 2015

(54) ULTRASONIC DIAGNOSIS APPARATUS, IMAGE PROCESSING APPARATUS, CONTROL METHOD FOR ULTRASONIC DIAGNOSIS APPARATUS, AND IMAGE PROCESSING METHOD

(75) Inventor: Ryota Osumi, Nasushiobara (JP)

(73) Assignees: KABUSHIKI KAISHA TOSHIBA, Tokyo (JP); Toshiba Medical Systems Corporation, Otawara-shi (JP)

(*) Notice: Subject to any disclaimer, the term of this patent is extended or adjusted under 35 U.S.C. 154(b) by 627 days.

(21) Appl. No.: 12/716,601

(22) Filed: Mar. 3, 2010

(65) Prior Publication Data

US 2010/0228129 A1  Sep. 9, 2010

(30) Foreign Application Priority Data

Mar. 4, 2009  (JP) .................................. 2009-051145

(51) Int. Cl.
*A61B 8/14* (2006.01)
*A61B 8/00* (2006.01)
*A61B 8/08* (2006.01)
*G06T 5/00* (2006.01)
(Continued)

(52) U.S. Cl.
CPC ................. *A61B 8/14* (2013.01); *A61B 8/4483* (2013.01); *A61B 8/483* (2013.01); *G06T 5/002* (2013.01); *G06T 5/003* (2013.01); *G06T 5/10* (2013.01); *G01S 7/52077* (2013.01); *G06T 2207/10136* (2013.01); *G06T 2207/20016* (2013.01); *G06T 2207/20064* (2013.01); *G06T 2207/20192* (2013.01)

(58) Field of Classification Search
USPC .......................................... 600/407, 437–475
See application file for complete search history.

(56) References Cited

U.S. PATENT DOCUMENTS 6,806,705 B2 * 10/2004 van Muiswinkel et al. .. 324/307
8,202,221 B2 * 6/2012 Osumi et al. ................. 600/443
(Continued)

FOREIGN PATENT DOCUMENTS

CN   1493258 A   5/2004
JP   2006-116307 A   5/2006
(Continued)

OTHER PUBLICATIONS

Khaled Z. Abd-Elmoniem, et al., "Real-Time Speckle Reduction and Coherence Enhancement in Ultrasound Imaging via Nonlinear Anisotropic Diffusion" IEEE Transactions on Biomedical Engineering, vol. 49. No. 9, Sep. 2002, pp. 997-1014.

Zeyun Yu, et al., "A Structure Tensor Approach for 3D Image Skeletonization: Applications in Protein Secondary Structure Analysis", Image Processing, IEEE International Conference, 2006, 4 pages.

(Continued)

*Primary Examiner* — Mark Remaly
(74) *Attorney, Agent, or Firm* — Oblon, McClelland, Maier & Neustadt, L.L.P.

(57) ABSTRACT

A transmission/reception unit transmits an ultrasonic wave to a subject via the ultrasonic probe, receives an ultrasonic wave reflected by the subject, and outputs an echo signal corresponding to the received ultrasonic wave. A first volume data generating unit generates first volume data based on the echo signal. A second volume data generating unit generates second volume data by applying, to each voxel contained in the first volume data, three-dimensional filtering with a filtering characteristic corresponding to three-dimensional directivity of the voxel. An image data generating unit generates data of a two-dimensional ultrasonic image based on the second volume data.

32 Claims, 6 Drawing Sheets

(51) Int. Cl.
*G06T 5/10* (2006.01)
*G01S 7/52* (2006.01)

(56) References Cited

U.S. PATENT DOCUMENTS

2006/0084869 A1 4/2006 Kim et al.
2009/0171208 A1 7/2009 Osumi et al.

FOREIGN PATENT DOCUMENTS

JP 2006-204912 A 8/2006
WO WO 2008/140043 A1 11/2008

OTHER PUBLICATIONS

Office Action issued on Jan. 7, 2014 in the corresponding Japanese Patent Application No. 2010-045682 (with English Translation).

Shigeru Muraki, "Wavelet and Computer Graphics", Nippon Steel Sumikin Research Institute Corporation, No. 4, vol. 16, Dec. 15, 1997, 11 Pages (with English Abstract).

Notification of the Second Office Action issued Jan. 18, 2012 in Chinese Patent Application No. 201010128835.7 (with English translation).

* cited by examiner

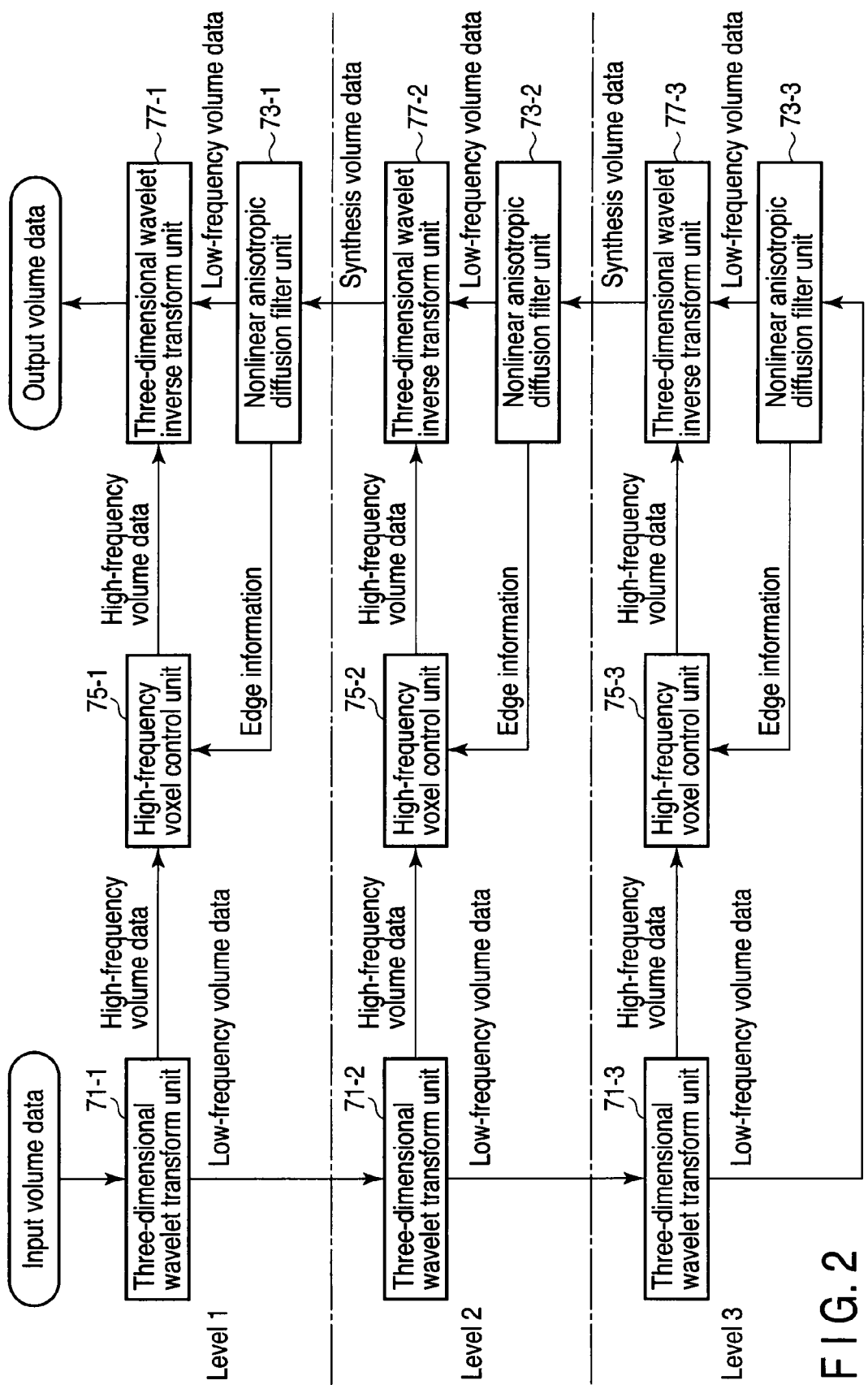
F I G. 2

| | x direction | y direction | z direction |
|---|---|---|---|
| DV1 | L | L | L |
| DV2 | H | L | L |
| DV3 | L | H | L |
| DV4 | H | H | L |
| DV5 | L | L | H |
| DV6 | H | L | H |
| DV7 | L | H | H |
| DV8 | H | H | H |

L: low frequency
H: high frequency $\lambda_{S1} \gg \lambda_{S2} \fallingdotseq \lambda_{S3}$
- Planes
- Anisotropy $\lambda_{S1} \fallingdotseq \lambda_{S2} \gg \lambda_{S3}$
- Lines
- Anisotropy $\lambda_{S1} \fallingdotseq \lambda_{S2} \fallingdotseq \lambda_{S3}$
- Spheres
- Isotropy

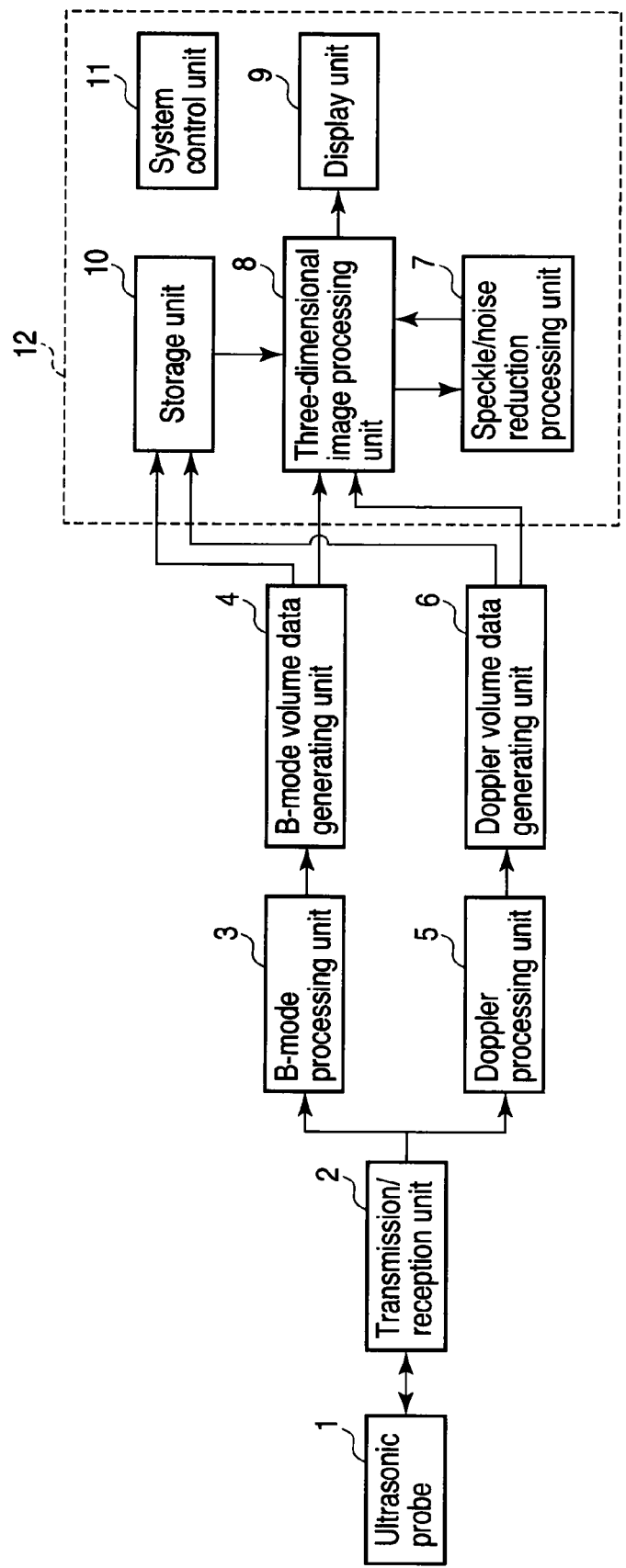
F I G. 9

ULTRASONIC DIAGNOSIS APPARATUS, IMAGE PROCESSING APPARATUS, CONTROL METHOD FOR ULTRASONIC DIAGNOSIS APPARATUS, AND IMAGE PROCESSING METHOD

CROSS-REFERENCE TO RELATED APPLICATIONS

This application is based upon and claims the benefit of priority from prior Japanese Patent Application No. 2009-051145, filed Mar. 4, 2009, the entire contents of which are incorporated herein by reference.

BACKGROUND OF THE INVENTION

1. Field of the Invention

The present invention relates to an ultrasonic diagnosis apparatus, an image processing apparatus, a control method for the ultrasonic diagnosis apparatus, and an image processing method which reduce speckle and noise contained in volume data.

2. Description of the Related Art

An ultrasonic diagnosis apparatus applies the ultrasonic pulses generated from the transducers incorporated in an ultrasonic probe into a subject, and receives the ultrasonic waves reflected by the subject through the transducers. The ultrasonic diagnosis apparatus then generates an echo signal corresponding to the received ultrasonic waves, generates ultrasonic image data based on the generated echo signal, and displays an ultrasonic image. In general, the ultrasonic diagnosis apparatus acquires a two-dimensional ultrasonic image by scanning a cross-section of a subject using an ultrasonic probe including a plurality of transducers arrayed one-dimensionally. Some recent ultrasonic diagnosis apparatuses can acquire a three-dimensional ultrasonic image (volume data) by scanning a volume in a subject using an ultrasonic probe or the like which includes a plurality of transducers arrayed two-dimensionally.

The ultrasonic waves reflected by a plurality of nearby subject tissues interfere with each other due to their phases. This interference produces an image pattern which differs in appearance from that obtained by synthesis only amplitudes, i.e., speckle. Speckle hinders the accurate observation of the position and shape of the boundary of a subject tissue. For this reason, various types of processing methods for the reduction of speckle have been proposed.

As described in, for example, the first reference (Jpn. Pat. Appln. KOKAI Publication No. 2006-116307), there has been proposed a method of performing multiresolution analysis of an ultrasonic image by wavelet transform/inverse transform or the like, detecting an edge of the image at each level, calculating the direction of an edge for each pixel, and performing smoothing in the tangential direction of each edge and filtering for sharpening in the normal direction of each edge. However, the application of this technique in the first reference is limited to two-dimensional ultrasonic images.

A method using a structure tensor is available as a method of performing structural analysis of a pixel region in image data as disclosed in the second reference (K. Z. Abd-Elmoniem, A. M. Youssef, and Y. M. Kadah, "Real-Time Speckle Reduction and Coherence Enhancement in Ultrasound Imaging via Nonlinear Anisotropic Diffusion", IEEE transactions on biomedical engineering, vol. 49, NO. 9, September 2002). The second reference discloses the application of a nonlinear anisotropic diffusion filter to the reduction of speckle on an ultrasonic image. However, the application of the second reference is also limited to two-dimensional ultrasonic images.

Note that it is possible to reduce speckle in volume data by dividing the volume data into cross-sections perpendicular to specific coordinate axes and applying a two-dimensional speckle reduction filter to each cross-section. In this case, however, as compared with the speckle reduction accuracy on a given surface to which a two-dimensional filter is applied, the speckle reduction accuracy on two surfaces vertically intersecting the given surface is low.

When three-dimensionally extending a nonlinear anisotropic diffusion filter, it is necessary to classify the characteristics of structures according to the magnitude relationship between the three eigenvalues of a three-dimensional structure tensor. The third reference (Z. Yu, C. Bajaj, "A Structure Tensor Approach for 3D Image Skeletonization: Applications in Protein Secondary Structure Analysis, Image Processing, 2006 IEEE International Conference on, 2006) discloses a concrete example of this technique. The third reference, however, does not disclose any method of linking each eigenvalue of a three-dimensional structure tensor to a three-dimensional diffusion equation.

BRIEF SUMMARY OF THE INVENTION

It is an object of the present invention to provide an ultrasonic diagnosis apparatus, an image processing apparatus, a control method for the ultrasonic diagnosis apparatus, and an image processing method which improve the reduction accuracy of speckle and noise contained in volume data and increase the reduction processing speed.

According to a first aspect of the present invention, there is provided an ultrasonic diagnosis apparatus including: an ultrasonic probe; a transmission/reception unit configured to transmit an ultrasonic wave to a subject via the ultrasonic probe and receive an echo signal corresponding to an ultrasonic wave reflected by the subject; a first volume data generating unit configured to generate first volume data based on the received echo signal; a low-frequency/high-frequency volume data generating unit configured to generate low-frequency volume data and high-frequency volume data on spatial frequencies based on the generated first volume data; a filter unit configured to calculate three eigenvalues for classifying three-dimensional structure patterns of three-dimensional structures contained in the generated low-frequency volume data, calculate edge information based on two eigenvalues of the three eigenvalues, and apply a nonlinear anisotropic diffusion filter having a filter characteristic corresponding to the calculated edge information to the low-frequency volume data; a high-frequency voxel control unit configured to perform edge enhancement processing for the high-frequency volume data based on the generated edge information; and a second volume data generating unit configured to generate second volume data with reduced speckle and reduced noise based on the low-frequency volume data to which the nonlinear anisotropic diffusion filter is applied by the filter unit and the high-frequency volume data for which edge enhancement processing is performed by the high-frequency voxel control unit.

According to a second aspect of the present invention, there is provided an ultrasonic diagnosis apparatus including: an ultrasonic probe; a transmission/reception unit configured to transmit an ultrasonic wave to a subject via the ultrasonic probe, receive an ultrasonic wave reflected by the subject, and output an echo signal corresponding to the received ultrasonic wave; a first volume data generating unit configured to generate first volume data based on the echo signal; a second volume data generating unit configured to generate second volume data by applying, to each voxel contained in the first volume data, three-dimensional filtering with a filtering characteristic corresponding to three-dimensional directivity of the voxel; and an image data generating unit configured to generate data of a two-dimensional ultrasonic image based on the second volume data.

According to a third aspect of the present invention, there is provided an ultrasonic diagnosis apparatus including: an ultrasonic probe; a transmission/reception unit configured to transmit an ultrasonic wave to a subject via the ultrasonic probe, receive an ultrasonic wave reflected by the subject, and output an echo signal corresponding to the received ultrasonic wave; a generating unit configured to generate first volume data based on the echo signal; a reduction unit configured to generate second volume data from the first volume data by reducing a three-dimensional isotropic structure component and enhancing a three-dimensional anisotropic structure component, the three-dimensional isotropic structure component and the three-dimensional anisotropic structure component being contained in the first volume data; and a three-dimensional image processing unit configured to generate data of a two-dimensional ultrasonic image by performing three-dimensional image processing for the second volume data.

According to a forth aspect of the present invention, there is provided an image processing apparatus including: a storage unit configured to store first volume data associated with a subject; a second volume data generating unit configured to generate second volume data by applying, to each voxel contained in the first volume data, three-dimensional filtering with a filtering characteristic corresponding to three-dimensional directivity of the voxel; and an image data generating unit configured to generate data of a two-dimensional ultrasonic image based on the second volume data.

According to a fifth aspect of the present invention, there is provided an image processing apparatus including: a storage unit configured to store first volume data associated with a subject; a reduction unit configured to generate second volume data from the first volume data by reducing a three-dimensional isotropic structure component and enhancing a three-dimensional anisotropic structure component, the three-dimensional isotropic structure component and the three-dimensional anisotropic structure component being contained in the first volume data; and a three-dimensional image processing unit configured to generate data of a two-dimensional image by performing three-dimensional image processing for the second volume data.

According to a sixth aspect of the present invention, there is provided a control method for the ultrasonic diagnosis apparatus, the ultrasonic diagnosis apparatus which includes an ultrasonic probe, a transmission/reception unit configured to transmit and receive a ultrasonic wave via the ultrasonic probe, a first volume data generating unit configured to generate a first volume data, a low-frequency/high-frequency volume data generating unit configured to generate a low-frequency volume data and a high-frequency volume data, a filter unit configured to adapt filter, a high-frequency voxel control unit configured to control a high-frequency voxel, a second volume data generating unit configured to generate a second volume data, and system control unit, the system control unit controlling: the transmission/reception unit to transmit an ultrasonic wave to a subject via the ultrasonic probe, receive an ultrasonic wave reflected by the subject via the ultrasonic probe, and output an echo signal corresponding to the received ultrasonic wave; the first volume data generating unit to generate first volume data based on the received echo signal; the low-frequency/high-frequency volume data generating unit to generate low-frequency volume data and high-frequency volume data on spatial frequencies based on the generated first volume data; the filter unit to calculate three eigenvalues for classifying three-dimensional structure patterns of three-dimensional structures contained in the generated low-frequency volume data, calculate edge information based on two eigenvalues of the three eigenvalues, and apply a nonlinear anisotropic diffusion filter having a filter characteristic corresponding to the calculated edge information to the low-frequency volume data; the high-frequency voxel control unit to perform edge enhancement processing for the high-frequency volume data based on the generated edge information; and the second volume data generating unit to generate second volume data with reduced speckle and reduced noise based on the low-frequency volume data to which the nonlinear anisotropic diffusion filter is applied by the filter unit and the high-frequency volume data for which edge enhancement processing is performed by the high-frequency voxel control unit.

According to a seventh aspect of the present invention, there is provided a control method for the ultrasonic diagnosis apparatus, the ultrasonic diagnosis apparatus includes an ultrasonic probe, a transmission/reception unit configured to transmit and receive a ultrasonic wave via the ultrasonic probe, a first volume data generating unit configured to generate a first volume data, a second volume data generating unit configured to generate a second volume data, a three-dimensional image processing unit configured to perform three-dimensional image processing unit, and system control unit, the system control unit controlling: the transmission/reception unit to transmit an ultrasonic wave to a subject via the ultrasonic probe, receive an ultrasonic wave reflected by the subject via the ultrasonic probe, and output an echo signal corresponding to the received ultrasonic wave; the first volume data generating unit to generate first volume data based on the output echo signal; the second volume data generating unit to generate second volume data by applying, to each voxel contained in the first volume data, three-dimensional filtering with a filtering characteristic corresponding to three-dimensional directivity of the voxel; and the three-dimensional image processing unit to generate data of a two-dimensional ultrasonic image based on the second volume data.

According to a eighth aspect of the present invention, there is provided an image processing method including: generating low-frequency volume data and high-frequency volume data on spatial frequencies based on first volume data associated with a subject; calculating three eigenvalues for classifying three-dimensional structure patterns of three-dimensional structures contained in the generated low-frequency volume data; calculating edge information based on two eigenvalues of the three eigenvalues; applying a nonlinear anisotropic diffusion filter having a filter characteristic corresponding to the calculated edge information to the low-frequency volume data; performing edge enhancement processing for the high-frequency volume data based on the generated edge information; and generating second volume data with reduced speckle and reduced noise based on the low-frequency volume data to which the nonlinear anisotropic diffusion filter is applied and the high-frequency volume data for which edge enhancement processing is performed.

According to a ninth aspect of the present invention, there is provided an image processing method including: generating second volume data by applying, to each voxel contained in the generated first volume data associated with a subject, three-dimensional filtering with a filtering characteristic corresponding to three-dimensional directivity of the voxel; and generating data of a two-dimensional image based on the second volume data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a view showing the arrangement of a speckle/noise reduction processing unit in FIG. 1;

FIG. 9 is a block diagram showing the arrangement of an ultrasonic diagnosis apparatus according to the first modification of this embodiment.

DETAILED DESCRIPTION OF THE INVENTION

An ultrasonic diagnosis apparatus, an image processing apparatus, a control method for the ultrasonic diagnosis apparatus, and an image processing method according to an embodiment of the present invention will be described below with reference to the views of the accompanying drawing.

Figure 1:
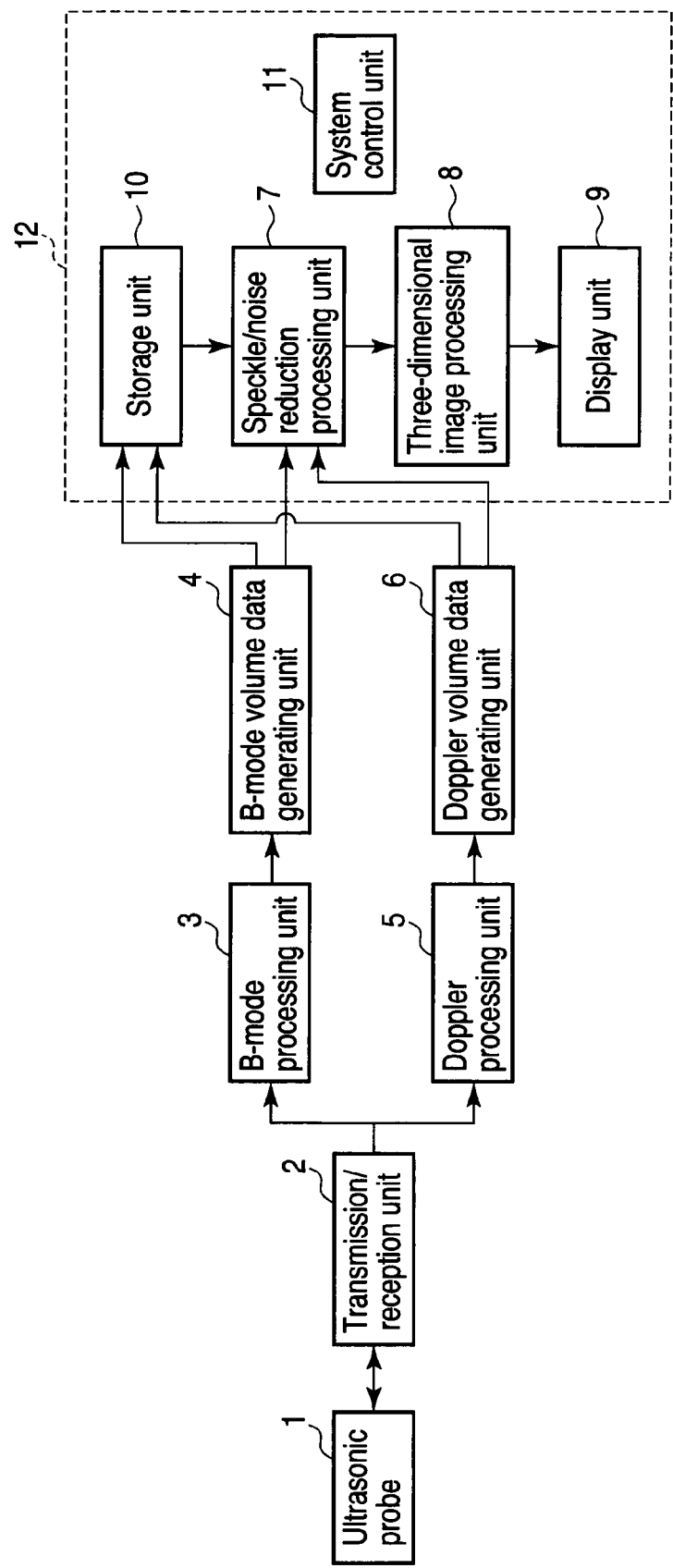
FIG. 1 is a block diagram showing the arrangement of an ultrasonic diagnosis apparatus according to an embodiment of the present invention.

FIG. 1 is a block diagram showing the arrangement of the ultrasonic diagnosis apparatus according to this embodiment. As shown in FIG. 1, this ultrasonic diagnosis apparatus includes an ultrasonic probe 1, a transmission/reception unit 2, a B-mode processing unit 3, a B-mode volume data generating unit 4, a Doppler processing unit 5, a Doppler volume data generating unit 6, a speckle/noise reduction processing unit 7, a three-dimensional image processing unit 8, and a display unit 9.

The ultrasonic probe 1 includes a plurality of transducers arrayed two-dimensionally. The ultrasonic probe 1 receives a driving signal from the transmission/reception unit 2 and transmits ultrasonic waves to a subject. The ultrasonic waves transmitted to the subject are sequentially reflected by an acoustic-impedance discontinuity surface in an internal body tissue. The ultrasonic probe 1 receives the reflected ultrasonic waves as an echo signal. The amplitude of this echo signal depends on an acoustic impedance difference on the discontinuity surface by which the echo signal is reflected. When the transmitted ultrasonic waves are reflected by the surface of a moving subject such as a moving blood flow or a cardiac wall, the echo signal is subjected to a frequency shift depending on the velocity component of the moving subject in the ultrasonic transmission direction due to a Doppler effect. Note that the ultrasonic probe 1 need not always be a two-dimensional array type probe as long as it can perform three-dimensional scanning. For example, the ultrasonic probe 1 may be a one-dimensional array type probe which can be mechanically swung.

The transmission/reception unit 2 repeatedly performs three-dimensional scanning of a volume to be scanned in the subject through the ultrasonic probe 1. As a result of this three-dimensional scanning, the transmission/reception unit 2 outputs a plurality of echo signals associated with a plurality of scanning lines associated with the scanned volume.

More specifically, the transmission/reception unit 2 includes a rate pulse generating circuit, transmission delay circuit, and driving pulse generating circuit (none of which are shown) for the transmission of ultrasonic waves. The rate pulse generating circuit repeatedly generates rate pulses for each channel at a predetermined rate frequency fr Hz (period: 1/fr sec). The delay circuit gives each rate pulse the delay time required to focus an ultrasonic wave into a beam and determine transmission directivity for each channel. The driving pulse generating circuit applies a driving pulse to the ultrasonic probe 1 at the timing based on each delayed rate pulse.

The transmission/reception unit 2 includes an amplifier circuit, A/D converter, reception delay circuit, and adder (none of which are shown) for the reception of ultrasonic waves. The amplifier circuit receives echo signals from the ultrasonic probe 1 and amplifies the received echo signals on a channel basis. The A/D converter converts the amplified echo signals from analog signals to digital signals on a channel basis. The reception delay circuit gives each echo signal converted into a digital signal the delay time required to focus the signal into a beam and determine reception directivity for each channel. The adder then adds the respective echo signals to which the delay times are given. With this addition processing, a reflection component from a direction corresponding to the reception directivity of an echo signal is enhanced to form an ultrasonic beam in accordance with the reception directivity and the transmission directivity. One ultrasonic beam corresponds to one ultrasonic scanning line. An echo signal for each scanning line is supplied to the B-mode processing unit 3 and the Doppler processing unit 5.

The B-mode processing unit 3 logarithmically amplifies the echo signals from the transmission/reception unit 2 and detects the envelope of the logarithmically amplified echo signals to generate the data of B-mode signals representing the intensities of the echo signals with luminances. The data of the generated B-mode signals are supplied to the B-mode volume data generating unit 4.

The B-mode volume data generating unit 4 generates volume data (to be referred to as B-mode volume data hereinafter) associated with the subject based on the B-mode signals from the B-mode processing unit 3. More specifically, the B-mode volume data generating unit 4 three-dimensionally arranges the data of the B-mode signals in a memory in accordance with the position information of each scanning line, and interpolates the data of B-mode signals between the scanning lines. This arrangement processing and interpolation processing generate B-mode volume data constituted by a plurality of voxels. Each voxel has a voxel value corresponding to the intensity of the data of the corresponding B-mode signal. The generated B-mode volume data is supplied to the speckle/noise reduction processing unit 7.

The Doppler processing unit 5 frequency-analyzes each echo signal from the transmission/reception unit 2 to extract a blood flow, tissue, and contrast medium echo component by the Doppler effect, and generates the data of a Doppler signal expressing the intensity of blood flow information such as an average velocity, variance, and power in color. The generated data of the Doppler signal is supplied to the Doppler volume data generating unit 6.

The Doppler volume data generating unit 6 generates volume data (to be referred to as Doppler volume data hereinafter) associated with the subject based on each Doppler signal from the Doppler processing unit 5. More specifically, the Doppler volume data generating unit 6 three-dimensionally arranges the data of the Doppler signals in the memory in accordance with the position information of each scanning line, and interpolates the data of Doppler signals between the scanning lines. This arrangement processing and interpolation processing generate Doppler volume data constituted by a plurality of voxels. Each voxel has a voxel value corresponding to the intensity of the data of the corresponding Doppler signal. The generated Doppler volume data is supplied to the speckle/noise reduction processing unit 7.

The speckle/noise reduction processing unit 7 executes speckle/noise reduction processing for each B-mode volume data from the B-mode volume data generating unit 4 and each Doppler volume data from the Doppler volume data generating unit 6 to generate B-mode volume data and Doppler volume data in which speckle and noise are reduced. More specifically, the speckle/noise reduction processing unit 7 reduces components having three-dimensional isotropic structures and contained in B-mode volume data and Doppler volume data, and enhances components having three-dimensional anisotropic structures, thereby reducing speckle and noise in these volume data. The B-mode volume data and Doppler volume data in which speckle and noise are reduced are supplied to the three-dimensional image processing unit 8. The speckle/noise reduction processing unit 7 will be described in detail later. Note that the speckle/noise reduction processing unit 7 need not perform speckle reduction processing for both B-mode volume data and Doppler volume data, and may perform it for only either of the data.

The three-dimensional image processing unit 8 generates the data of a two-dimensional B-mode image by performing three-dimensional image processing for the B-mode volume data from the speckle/noise reduction processing unit 7. The three-dimensional image processing unit 8 also generates the data of a two-dimensional Doppler image by performing three-dimensional image processing for the Doppler volume data from the speckle/noise reduction processing unit 7. The three-dimensional image processing to be used includes MPR (Multi Planar Reconstruction) processing, CPR (Curved Planar Reconstruction) processing, SPR (Stretched CPR) processing, volume rendering, surface rendering, and MIP (Maximum Intensity Projection). The generated B-mode image data and Doppler image data are supplied to the display unit 9.

The display unit 9 displays the B-mode image from the three-dimensional image processing unit 8. The display unit 9 also displays the Doppler image from the three-dimensional image processing unit. The display unit 9 may display the B-mode image and the Doppler image while superimposing the Doppler image on the B-mode image. As the display unit 9, for example, a display device such as a CRT display, liquid crystal display, organic electroluminescence display, plasma display, or the like can be used as needed.

The ultrasonic diagnosis apparatus further includes a storage unit 10. The storage unit 10 stores B-mode volume data from the B-mode volume data generating unit 4 and Doppler volume data from the Doppler volume data generating unit 6. The speckle/noise reduction processing unit 7 reads out the B-mode volume data and Doppler volume data stored in the storage unit 10, and supplies them for speckle/noise reduction processing.

The ultrasonic diagnosis apparatus further includes a system control unit 11. The system control unit 11 controls the respective units of the ultrasonic diagnosis apparatus. For example, the system control unit 11 the respective units to performing a speckle/noise reduction processing which characterizes this embodiment.

The speckle/noise reduction processing unit 7, the three-dimensional image processing unit 8, the display unit 9, storage unit 10, and system control unit 11 constitute an image processing apparatus 12. The image processing apparatus 12 is typically a computer incorporated in the ultrasonic diagnosis apparatus according to this embodiment.

Speckle/noise reduction processing executed by the speckle/noise reduction processing unit 7 will be described in detail next. As described above, the speckle/noise reduction processing unit 7 can perform speckle reduction processing for B-mode volume data and Doppler volume data. For the sake of descriptive simplicity, B-mode volume data and Doppler volume data will not be discriminated from each other and will be simply called volume data hereinafter. When a B-mode image and a Doppler image are not specifically discriminated from each other, they are called ultrasonic images.

The speckle/noise reduction processing unit 7 applies three-dimensional filtering to each voxel contained in volume data with a filtering characteristic corresponding to the three-dimensional directivity of the voxel. The speckle/noise reduction processing unit 7 reduces component having a three-dimensional isotropic structure contained in volume data, and enhances component having a three-dimensional anisotropic structure in the volume data. Note that speckle/noise reduction processing need not always be performed for both a three-dimensional isotropic structure component and a three-dimensional anisotropic structure component. That is, the speckle/noise reduction processing unit 7 may only either reduce three-dimensional isotropic structure components or enhance three-dimensional anisotropic structure components.

FIG. 2 is a view showing the arrangement of the speckle/noise reduction processing unit 7. As shown in FIG. 2, the speckle/noise reduction processing unit 7 has a multiple structure constituted by a plurality of layers to perform multiresolution analysis/synthesis. In this embodiment, the highest degree of multiresolution analysis/synthesis is level 3. However, the embodiment need not be limited to this. That is, it is possible to perform multiresolution analysis/synthesis in the range of the first level to the nth level (where n is a natural number equal to or more than two). The embodiment uses wavelet transform/inverse transform as an example of multiresolution analysis/synthesis. However, the embodiment need not be limited to this. For example, it is possible to use an existing multiresolution analysis/synthesis method such as the Laplacian pyramid method or Gabor transform/inverse transform as multiresolution analysis/synthesis. Wavelet transform/inverse transform in the embodiment indicates so-called discrete wavelet transform/inverse transform.

The speckle/noise reduction processing unit 7 includes, at the respective layers, three-dimensional wavelet transform units 71, i.e., 71-1, 71-2, and 71-3, nonlinear anisotropic diffusion filter units 73, i.e., 73-1, 73-2, and 73-3, high-frequency voxel control units 75, i.e., 75-1, 75-2, and 75-2, and three-dimensional wavelet inverse transform units 77, i.e., 77-1, 77-2, and 77-3.

Each three-dimensional wavelet transform unit 71 analyses input volume data into one type of low-frequency volume data and seven types of high-frequency volume data by applying three-dimensional wavelet transform to the input volume data.

Figures 3, 4:
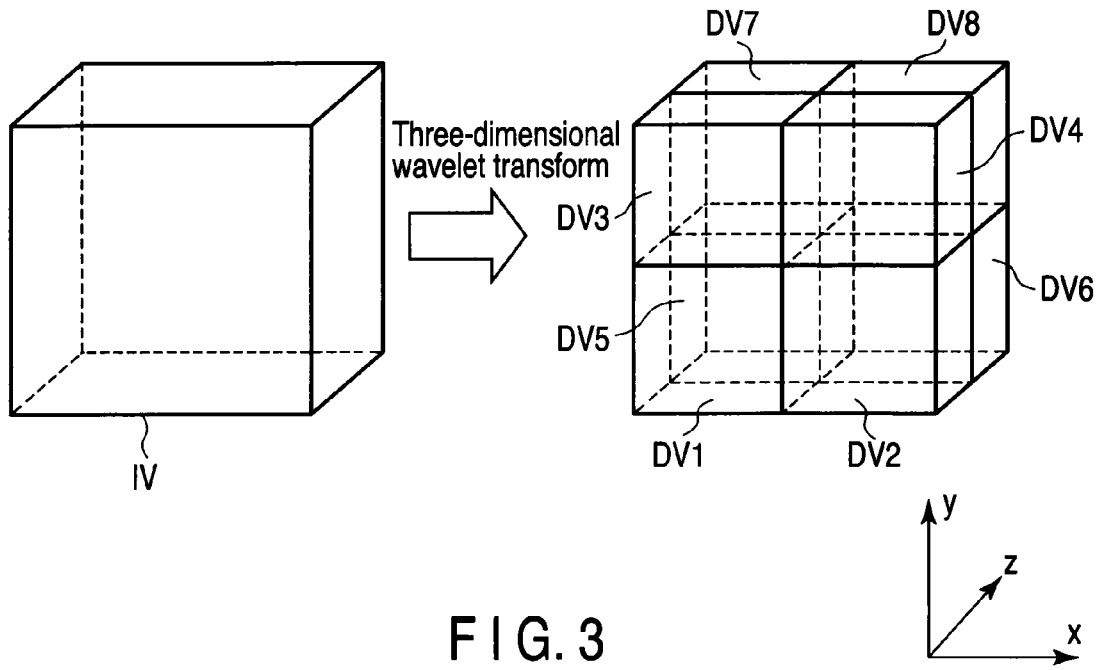
FIG. 3 is a perspective view showing a concept of three-dimensional wavelet transform by a three-dimensional wavelet transform unit in FIG. 2.
FIG. 4 is a view showing an application pattern of a filter applied in each coordinate axis direction in wavelet transform in FIG. 3.

FIG. 3 is a conceptual view of multiresolution analysis by three-dimensional wavelet transform. FIG. 4 is a view showing an application pattern of a filter applied in each coordinate axis direction in three-dimensional wavelet transform. As shown in FIGS. 3 and 4, volume data IV is wavelet-transformed by applying a one-dimensional low-pass (L) filter and high-pass (H) filter to the volume data IV before analysis in each axis direction in an xyz orthogonal coordinate system. Such three-dimensional wavelet transform analyses the volume data IV into one type of low-frequency volume data DV1 and seven types of high-frequency volume data DV2 to DV8. The low-frequency volume data DV1 contains low-frequency components of the spatial frequency components which the volume data IV has. The high-frequency volume data DV2 to DV8 each contain a high-frequency component, in at least one direction, of the spatial frequency components which the volume data IV has. For example, applying a low-pass filter to the x-, y-, and z-axes will generate the low-frequency volume data DV1 having only low-frequency components in the x-, y-, and z-axis directions. Another example is that the high-frequency volume data DV2 containing an enhanced high-frequency component in the x-axis direction is generated by applying a high-pass filter to the x-axis and applying a low-pass filter to each of the y- and z-axes. The number of samples per coordinate axis of each of the volume data DV1 to DV8 after analysis is reduced to half the number of samples per coordinate axis of the volume data IV before analysis.

If the three-dimensional wavelet transform unit 71 does not belong to the highest layer (level 3), the generated low-frequency volume data is supplied to the three-dimensional wavelet transform unit 71 at one layer higher. If the three-dimensional wavelet transform unit 71 belongs to the highest layer, the generated low-frequency volume data is supplied to the nonlinear anisotropic diffusion filter unit 73 at the same highest layer. In addition, high-frequency volume data is supplied to the high-frequency voxel control unit 75 belonging to the same layer.

The nonlinear anisotropic diffusion filter unit 73 calculates information associated with the magnitude of an edge component contained in the supplied low-frequency volume data. Information associated with the magnitude of an edge component will be referred to as edge information hereinafter. The edge information is supplied to the high-frequency voxel control unit 75 at the same layer. The nonlinear anisotropic diffusion filter unit 73 also applies a three-dimensional nonlinear anisotropic diffusion filter to the supplied low-frequency volume data. The nonlinear anisotropic diffusion filter enhances the edge components contained in the low-frequency volume data and smoothes the non-edge components contained in the low-frequency volume data. The nonlinear anisotropic diffusion filter is a filter for enhancing nonlinearly and anisotropically diffused components. The edge components in low-frequency volume data are nonlinearly and anisotropically diffused. On the other hand, non-edge components represented by speckle and noise are non-linearly and isotropically diffused. Therefore, applying a nonlinear anisotropic diffusion filter to low-frequency volume data will increase the voxel values of edge components and reduce non-edge components. A nonlinear anisotropic diffusion filter according to this embodiment is designed to increase the processing speed while improving the speckle/noise reduction accuracy. This filter will be described later. Low-frequency volume data after filtering is supplied to the three-dimensional wavelet inverse transform unit 77 at the same layer.

The processing performed by each nonlinear anisotropic diffusion filter unit 73 will be described in detail below. The nonlinear anisotropic diffusion filter unit 73 applies, to low-frequency volume data, a nonlinear anisotropic diffusion filter which is a filter designed in consideration of the directivity of each structure (each voxel region) in the low-frequency volume data, and outputs edge information and filtered low-frequency volume data. The nonlinear anisotropic diffusion filter is represented by the following diffusion equation (partial differential equation) (1).

$$\frac{\partial I}{\partial t} = div[D\nabla I] \qquad (1)$$

where I is the voxel value of volume data to be processed, $\nabla I$ is the gradient vector of the volume data, and t is the time associated with the processing. In actual processing, t represents the number of times of processing of this diffusion equation. In this embodiment, the number of times t of processing is not specifically limited. For a concrete explanation, assume that the number of times t is one. D represents a diffusion tensor, which is expressed as follows:

$$D = \begin{pmatrix} d_{11} & d_{12} & d_{13} \\ d_{12} & d_{22} & d_{23} \\ d_{13} & d_{23} & d_{33} \end{pmatrix} = R \begin{pmatrix} \lambda_{D1} & 0 & 0 \\ 0 & \lambda_{D2} & 0 \\ 0 & 0 & \lambda_{D3} \end{pmatrix} R^T \qquad (2)$$

where $\lambda_{D1}$, $\lambda_{D2}$, and $\lambda_{D3}$ are the eigenvalues of the diffusion tensor D, and R is the eigenvector of the diffusion tensor D. The eigenvector R is represented by $$R=(\omega_1 \omega_2 \omega_3) \qquad (3)$$

The eigenvalue $\lambda_{D1}$ of the diffusion tensor D represents the intensity of diffusion in the direction indicated by an eigenvector $\omega_1$. Likewise, the eigenvalue $\lambda_{D2}$ represents the intensity of diffusion in the direction indicated by an eigenvector $\omega_2$, and the eigenvalue $\lambda_{D3}$ represents the intensity of diffusion in the direction indicated by an eigenvector $\omega_3$. Controlling the values of the eigenvalues $\lambda_{D1}$, $\lambda_{D2}$, and $\lambda_{D3}$ for each voxel will control the intensity of diffusion of the nonlinear anisotropic diffusion filter. Note that the eigenvector R is anonymous with the filter direction of the nonlinear anisotropic diffusion filter. Properly setting the eigenvector R will set a desired filter direction for the nonlinear anisotropic diffusion filter.

In addition, the eigenvectors $\omega_1$, $\omega_2$, and $\omega_3$ of the diffusion tensor D are equal to the eigenvectors of a three-dimensional structure tensor S of a voxel in low-frequency volume data. The eigenvalues $\lambda_{D1}$, $\lambda_{D2}$, and $\lambda_{D3}$ of the diffusion tensor D depend on the magnitude of the edge calculated from the eigenvalues of the three-dimensional structure tensor S (to be described later).

The three-dimensional structure tensor S is defined as follows:

$$S = G_\rho * \begin{pmatrix} I_x^2 & I_x I_y & I_x I_z \\ I_x I_y & I_y^2 & I_y I_z \\ I_x I_z & I_y I_z & I_z^2 \end{pmatrix} \quad (4)$$

$$= \begin{pmatrix} s_{11} & s_{12} & s_{13} \\ s_{12} & s_{22} & s_{23} \\ s_{13} & s_{23} & s_{33} \end{pmatrix}$$

$$= R \begin{pmatrix} \lambda_{S1} & 0 & 0 \\ 0 & \lambda_{S2} & 0 \\ 0 & 0 & \lambda_{S3} \end{pmatrix} R^T$$

where $I_x$ represents a spatial derivative along the x direction of volume data I to be processed, $I_y$ represents a spatial derivative along the y direction of the volume data I to be processed, $I_z$ represents a spatial derivative along the z direction of the volume data I to be processed, $G_\rho$ is a three-dimensional Gaussian function, and the operator "★" represents convolution. The eigenvalues $\lambda_{S1}$, $\lambda_{S2}$, and $\lambda_{S3}$ are the eigenvalues of the three-dimensional structure tensor S, which have a magnitude relationship of $\lambda_{S1} \geq \lambda_{S2} \geq \lambda_{S3}$. A method of calculating the spatial derivatives $I_x$, $I_y$, and $I_z$ need not strictly follow the above calculation method. For example, it is possible to use a Sobel filter or the high-frequency components obtained by multiresolution analysis instead of calculating $I_x$, $I_y$, and $I_z$.

The eigenvalues $\lambda_{S1}$, $\lambda_{S2}$, and $\lambda_{S3}$, the eigenvector R, and an eigenvector $R^T$ in a case in which each element s of the three-dimensional structure tensor S is obtained in advance can be calculated by a method known well in linear algebra. That is, it is practically possible to calculate eigenvalues $\lambda_{S1}$, $\lambda_{S2}$, and $\lambda_{S3}$ of the 3×3 matrix in equation (4) by solving a three-dimensional equation using, for example, the Cardano method. In addition, since the three-dimensional structure tensor S is a real symmetric matrix, the eigenvalues $\lambda_{S1}$, $\lambda_{S2}$, and $\lambda_{S3}$ are real numbers, and the eigenvectors R and $R^T$ are real vectors. The real vectors R and $R^T$ are perpendicular to each other.

Figure 5:
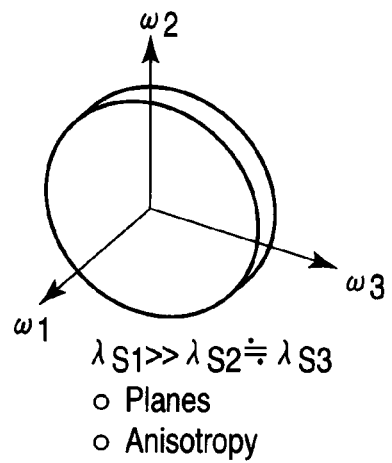
FIG. 5 is a view showing one of the three structure patterns classified according to the magnitude relationship between three eigenvalues of a three-dimensional structure tensor.
Figure 6:
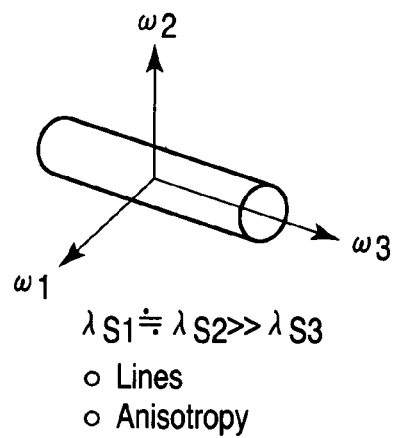
FIG. 6 is a view showing one of the three structure patterns classified according to the magnitude relationship between three eigenvalues of the three-dimensional structure tensor.
Figure 7:
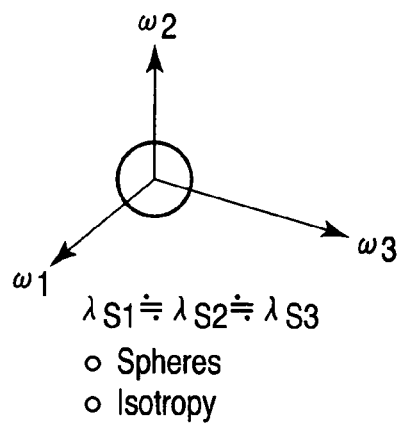
FIG. 7 is a view showing one of the three structure patterns classified according to the magnitude relationship between three eigenvalues of the three-dimensional structure tensor.

The representative structure patterns of the three-dimensional structures contained in volume data are classified according to the magnitude relationship between the eigenvalues $\lambda_{S1}$, $\lambda_{S2}$, and $\lambda_{S3}$ of the three-dimensional structure tensor S. FIGS. 5, 6, and 7 are schematic views each showing one of the three structure patterns. As shown in FIG. 5, in the case of $\lambda_{S1} \gg \lambda_{S2} \cong \lambda_{S3}$, the corresponding structure is an anisotropic structure, which has a planar structure. As shown in FIG. 6, in the case of $\lambda_{S1} \cong \lambda_{S2} \gg \lambda_{S3}$, the corresponding structure is an anisotropic structure, which has a linear structure. As shown in FIG. 7, in the case of $\lambda_{S1} \cong \lambda_{S2} \cong \lambda_{S3}$, the corresponding structure is an isotropic structure, which has a spherical structure. Speckle and noise to be reduced has a spherical structure. An edge component to be enhanced has a planar or linear structure.

The present inventor has empirically found that it is not necessary to specifically discriminate a planar structure from a linear structure when applying a nonlinear anisotropic diffusion filter to the three-dimensional structure tensor of volume data. This is because an ultrasonic image generated in consideration of the second eigenvalue $\lambda_{S2}$ exhibits no improvement in image quality as compared with an ultrasonic image generated without such consideration. For this reason, this embodiment will discriminate the shape of a three-dimensional structure in accordance with the difference value between the first eigenvalue $\lambda_{S1}$ and the third eigenvalue $\lambda_{S3}$. That is, in the case of difference value DI≫0, the corresponding structure is an anisotropic structure. In the case of DI≅0, the corresponding structure is an isotropic structure. The difference between the first eigenvalue $\lambda_{S1}$ and the third eigenvalue $\lambda_{S3}$ is used for the calculation of edge information. Edge information Pe is represented as follows:

$$Pe = 1 - \exp\left(-\frac{(\lambda_{S1} - \lambda_{S3})^2}{k^2}\right) \quad (5)$$

The edge information Pe is the parameter calculated by normalizing the magnitude of an edge in the range of 0 to 1. The nearer the value of the edge information Pe is to 1, the stronger the anisotropy is. The nearer the value of the edge information Pe is to 0, the stronger the isotropy is. That is, as the value of the edge information Pe approaches 1, the structure approaches an edge component, whereas as the value of the edge information Pe approaches 0, the structure approaches a non-edge component. As described above, the edge information Pe indicates the degree of anisotropy or isotropy (an edge component or non-edge component) of the structure.

The parameter k indicates the degree of extraction of an edge component. The user can arbitrarily set the parameter k via an operation unit (not shown). For example, decreasing the parameter k makes it easy to extract an edge component.

The edge information Pe is used to calculate the intensity of diffusion of the nonlinear anisotropic disffusion filter, i.e., the eigenvalues $\lambda_{D1}$, $\lambda_{D2}$, and $\lambda_{D3}$ of the diffusion tensor D. The eigenvalues $\lambda_{D1}$, $\lambda_{D2}$, and $\lambda_{D3}$ are respectively represented by equations (6), (7), and (8):

$$\lambda_{D1} = \beta_1(1-Pe) + \beta_2 \cdot Pe \quad (6)$$

$$\lambda_{D2} = \beta_2(1-Pe) + \beta_4 \cdot Pe \quad (7)$$

$$\lambda_{D3} = \beta_5(1-Pe) + \beta_6 \cdot Pe \quad (8)$$

In equations (6), (7), and (8), the portion of $\beta(1-Pe)$ represents a non-edge component, and the portion of $\beta \cdot Pe$ represents an edge component. It is necessary to make a non-edge component to which speckle or noise to be reduced belongs have no directivity. That is, it is necessary to diffuse this non-edge component regardless of directions. For this purpose, $\beta_1 = \beta_3 = \beta_5 > 0$ is set. On the other hand, it is necessary to further enhance the directivity of an edge component to be enhanced. That is, it is necessary to sharpen this edge component in the vertical direction (the direction indicated by the eigenvector $\omega_1$ of the eigenvalue $\lambda_{D1}$) and diffuse it in the remaining directions (the directions indicated by the eigenvectors $\omega_2$ and $\omega_3$ of the eigenvalues $\lambda_{D2}$ and $\lambda_{D3}$). For this purpose, $\beta_2$ is set to a value near 0, and $\beta_4$ and $\beta_6$ are set to predetermined values larger than $\beta_2$. It is possible to arbitrarily set the parameters $\beta_1$, $\beta_2$, $\beta_3$, $\beta_4$, $\beta_5$, and $\beta_6$ via the operation unit (not shown).

In addition, as described above, the eigenvectors $\omega_1$, $\omega_2$, and $\omega_3$ of the diffusion tensor D are equal to the eigenvectors $\omega_1$, $\omega_2$, and $\omega_3$ of the three-dimensional structure tensor S. It is therefore possible to calculate the eigenvalues $\lambda_{D1}$, $\lambda_{D2}$, and $\lambda_{D3}$ and eigenvectors $\omega_1$, $\omega_2$, and $\omega_3$ of the diffusion tensor D. That is, it is possible to calculate each element d of the diffusion tensor D in equation (2) and obtain a nonlinear anisotropic diffusion filter (diffusion equation (1)). As described above, the eigenvalues (the intensity of diffusion) of the nonlinear anisotropic diffusion filter according to this embodiment change in accordance with the magnitude of the edge information Pe indicating the degree of anisotropy or isotropy. That is, applying the nonlinear anisotropic diffusion filter according to this embodiment to low-frequency volume data will enhance components having anisotropic structures in the low-frequency volume data and reduce components having isotropic structures.

Figure 8:
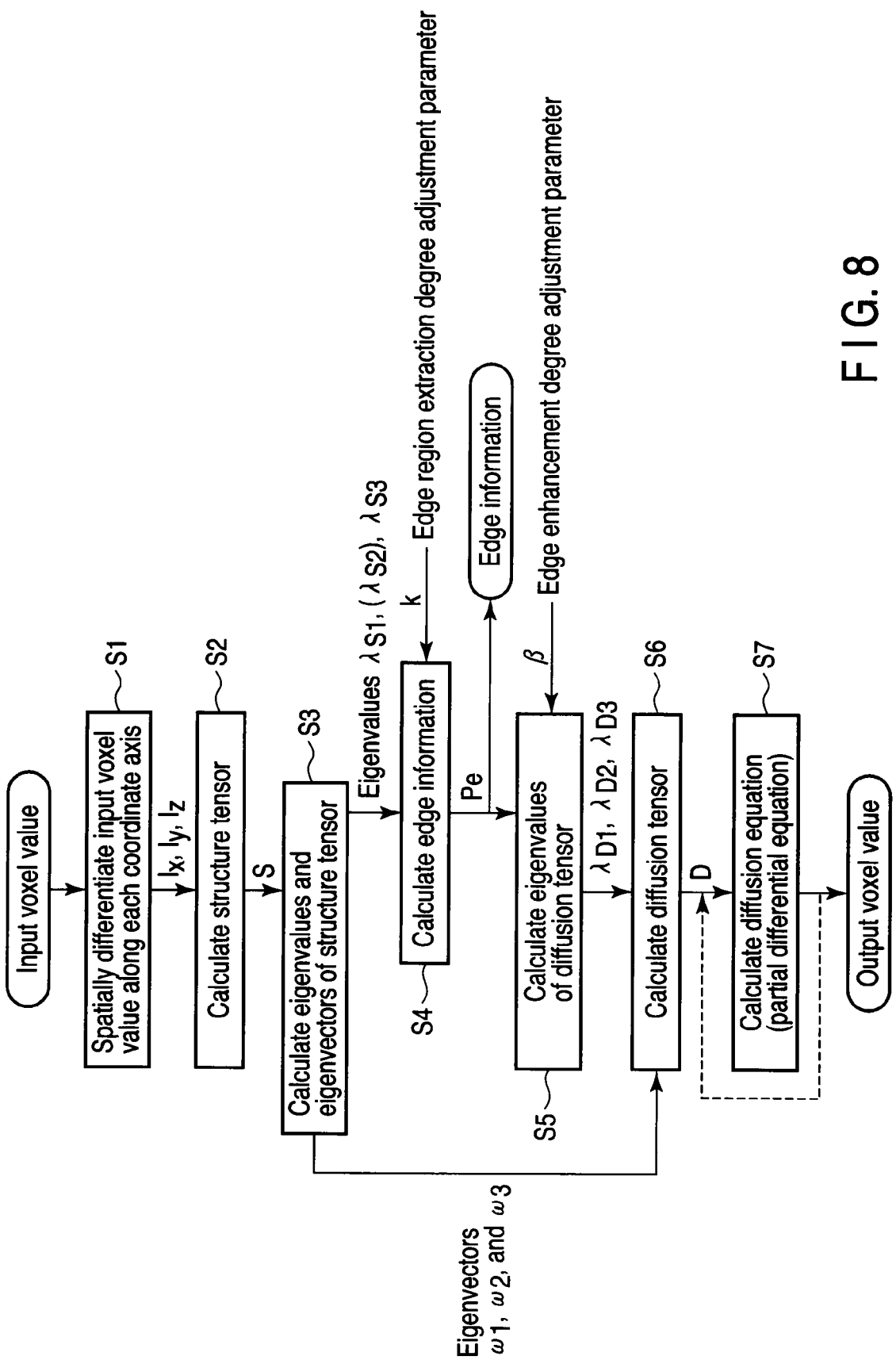
FIG. 8 is a flowchart showing a typical procedure for processing by a nonlinear anisotropic diffusion filter unit in FIG. 2.

FIG. 8 is a flowchart showing a typical procedure for filter processing by the nonlinear anisotropic diffusion filter unit 73. Note that the processing in steps S1 to S6 is performed for each voxel constituting volume data to be processed.

As shown in FIG. 8, first of all, the nonlinear anisotropic diffusion filter unit 73 receives the voxel value of an input voxel, to be processed, of low-frequency volume data. The nonlinear anisotropic diffusion filter unit 73 calculates derivative values I, i.e., $I_x$, $I_y$, and $I_z$, by spatially differentiating the voxel value of the input voxel along the respective coordinate axes based on the voxel value of the input voxel and the voxel values of neighboring voxels (step S1). Upon calculating the derivative values I, the nonlinear anisotropic diffusion filter unit 73 calculates each element s of the structure tensor S by convoluting the calculated derivative values I and the three-dimensional Gaussian function $G_\rho$ according to equation (4) (step S2). Note that the calculation in step S2 includes the calculation of the three-dimensional Gaussian function $G_\rho$.

Upon calculating each element s of the three-dimensional structure tensor S, the nonlinear anisotropic diffusion filter unit 73 calculates an eigenvalue $\lambda_s$ and eigenvector $\omega$ of the three-dimensional structure tensor S by performing linear algebra on each calculated element s according to equation (4) (step S3). Upon calculating the eigenvalue $\lambda_s$, the nonlinear anisotropic diffusion filter unit 73 calculates the edge information Pe by using the calculated eigenvalue $\lambda_s$ and the parameter k according to equation (5) (step S4). The edge information Pe is supplied to the high-frequency voxel control unit 75.

Upon calculating the edge information Pe, the nonlinear anisotropic diffusion filter unit 73 calculates the intensity of diffusion, i.e., the eigenvalues $\lambda_{D1}$, $\lambda_{D2}$, and $\lambda_{D3}$ of the diffusion tensor D by using the edge information Pe and a parameter β according to equations (6), (7), and (8) (step S5). Upon calculating the eigenvalues $\lambda_{D1}$, $\lambda_{D2}$, and $\lambda_{D3}$ of the diffusion tensor D and the eigenvectors $\omega_1$, $\omega_2$, and $\omega_3$ of the diffusion tensor D (structure tensor S), the nonlinear anisotropic diffusion filter unit 73 calculates each element d of the diffusion tensor D by performing linear algebra on the calculated eigenvalues $\lambda_{D1}$, $\lambda_{D2}$, and $\lambda_{D3}$ and the calculated eigenvectors $\omega_1$, $\omega_2$, and $\omega_3$ according to equation (2) (step S6). Upon calculating each element d of the diffusion tensor D, the nonlinear anisotropic diffusion filter unit 73 calculates an output voxel value by performing numerical analytic computation of diffusion equation (1) based on each calculated element d and the derivative values I (step S7). More specifically, based on the voxel values of a given voxel and its neighboring voxels and each element value of a diffusion tensor at time t, the nonlinear anisotropic diffusion filter unit 73 obtains the new voxel value of the given voxel at time t+Δt, and repeats similar calculation once to a few times upon setting t+Δt as new time t. The calculated output voxel value is supplied to the three-dimensional wavelet inverse transform unit 77.

Upon completing step S7, the nonlinear anisotropic diffusion filter unit 73 changes the input voxel to be processed to the next one, and performs steps S1 to S7 again. When steps S1 to S7 are performed for all the voxels of the input volume data to be processed, the filter processing by the nonlinear anisotropic diffusion filter unit 73 is terminated.

That is, the nonlinear anisotropic diffusion filter unit 73 applies a three-dimensional nonlinear anisotropic diffusion filter having the intensity of diffusion corresponding to the eigenvalues of a three-dimensional structure tensor to low-frequency volume data in the filtering directions corresponding to the eigenvectors of the three-dimensional structure tensor (the directions indicated by the eigenvectors of the diffusion tensor), thereby generating low-frequency volume data after filtering.

The high-frequency voxel control unit 75 controls the voxel value of each voxel contained in high-frequency volume data from the three-dimensional wavelet transform unit 71 based on edge information from the nonlinear anisotropic diffusion filter unit 73. More specifically, the high-frequency voxel control unit 75 increases the voxel value of each component having an anisotropic structure and contained in the high-frequency volume data, and decreases the voxel value of each component having an isotropic structure. That is, the high-frequency voxel control unit 75 reduces speckle and noise components contained in high-frequency volume data.

More specifically, the high-frequency voxel control unit 75 outputs an output voxel value $I_H'$ by applying a filter to an input voxel value $I_H$. This filter is represented by $$I'_H = A \cdot Pe \cdot I_H + B \cdot (1-Pe) \cdot I_H \qquad (9)$$

where A is a control coefficient for an edge component, and B is a control coefficient for a non-edge component represented by speckle or noise. For example, the control coefficient A is set to 1 or more, and the control coefficient B is set to 1 or less. That is, an edge component is enhanced by the product of $I_H$, A, and Pe. A non-edge component is reduced by the product of $I_H$, B, and (1−Pe). The high-frequency volume data in which edge components are enhanced and non-edge components are reduced by this filter is supplied to the three-dimensional wavelet inverse transform unit 77.

Setting A=0 and B≠0 will make the high-frequency voxel control unit 75 reduce non-edge components (isotropic structure components) without enhancing edge components (anisotropic structure components). Reducing the non-edge components in this manner can relatively enhance the edge components. In contrast, setting A≠0 and B=0 will make the high-frequency voxel control unit 75 enhance the edge components (anisotropic structure components) without reducing the non-edge components (isotropic structure components). Enhancing the edge components in this manner can relatively reduce the non-edge components.

The following method is another method of making the high-frequency voxel control unit 75 enhance edge components. First of all, the magnitude of predetermined edge information is set as a threshold. Each voxel having edge information which has value more than the threshold is set as an edge component. Each voxel having edge information which has value less than the threshold is set as a non-edge component. The high-frequency voxel control unit 75 changes the output voxel value of each voxel belonging to an edge component to the product of the input voxel value and the control coefficient A. In other words, the high-frequency voxel control unit 75 replaces the input voxel value of each voxel belonging to an edge component by the product of the input voxel value and the control coefficient A. In addition, the high-frequency voxel control unit 75 changes the output voxel value of each voxel belonging to a non-edge component to the product of the input voxel value and the control coefficient B. The high-frequency voxel control unit 75 replaces the input voxel value of each voxel belonging to a non-edge component by the product of the input voxel value and the control coefficient B.

The three-dimensional wavelet inverse transform unit 77 generates synthesis volume data by performing multiresolution synthesis (three-dimensional wavelet inverse transform as a typical example in this embodiment) of low-frequency volume data from the nonlinear anisotropic diffusion filter unit 73 and high-frequency volume data from the high-frequency voxel control unit 75 and synthesis the low-frequency volume data and the high-frequency volume data. As compared with the input volume data, the generated synthesis volume data contains enhanced components having anisotropic structures and reduced components having isotropic structures. The number of samples per coordinate axis of the generated synthesis volume data is increased double the number of samples per coordinate axis of the input volume data. If the three-dimensional wavelet inverse transform unit 77 does not belong to the lowest layer, the generated synthesis volume data is supplied to the nonlinear anisotropic diffusion filter unit 73 at one layer lower. If the three-dimensional wavelet inverse transform unit 77 belongs to the lowest layer, the generated synthesis volume data is supplied to the three-dimensional image processing unit 8.

Procedures for processing performed by the three-dimensional wavelet transform unit 71, nonlinear anisotropic diffusion filter unit 73, high-frequency voxel control unit 75, and three-dimensional wavelet inverse transform unit 77 at each layer will be described next.

As shown in FIG. 2, the three-dimensional wavelet transform unit 71-1 at level 1 performs three-dimensional wavelet transform for input volume data, and outputs one type of low-frequency volume data and seven types of high-frequency volume data. The low-frequency volume data is supplied to the three-dimensional wavelet transform unit 71-2 at level 2. The high-frequency volume data are supplied to the high-frequency voxel control unit 75-1 at level 1.

The three-dimensional wavelet transform unit 71-2 at level 2 performs three-dimensional wavelet transform for the low-frequency volume data from the three-dimensional wavelet transform unit 71-1 at level 1, and outputs one type of low-frequency volume data and seven types of high-frequency volume data. The low-frequency volume data is supplied to the three-dimensional wavelet transform unit 71-3 at level 3. The high-frequency volume data are supplied to the high-frequency voxel control unit 75-2 at level 2.

The three-dimensional wavelet transform unit 71-3 at level 3 performs three-dimensional wavelet transform for the low-frequency volume data from the three-dimensional wavelet transform unit 71-2 at level 2, and outputs one type of low-frequency volume data and seven types of high-frequency volume data. The low-frequency volume data is supplied to the nonlinear anisotropic diffusion filter unit 73-3 at level 3. The high-frequency volume data are supplied to the high-frequency voxel control unit 75-3 at level 3.

The nonlinear anisotropic diffusion filter unit 73-3 calculates edge information associated with the low-frequency volume data from the three-dimensional wavelet transform unit 71-3. The edge information is supplied to the high-frequency voxel control unit 75-3 at level 3. The nonlinear anisotropic diffusion filter unit 73-3 applies the nonlinear anisotropic diffusion filter to the low-frequency volume data. The low-frequency volume data after filtering is supplied to the three-dimensional wavelet inverse transform unit 77-3 at level 3.

The high-frequency voxel control unit 75-3 receives the seven types of high-frequency volume data from the three-dimensional wavelet transform unit 71-3 and the edge information from the nonlinear anisotropic diffusion filter unit 73-3. The high-frequency voxel control unit 75-3 then controls the voxel values of the voxels contained in each of the seven types of high-frequency volume data based on the input edge information, and outputs seven types of high-frequency volume data in which the voxel values are controlled. The seven types of high-frequency volume data are supplied to the three-dimensional wavelet inverse transform unit 77-3 at level 3.

The three-dimensional wavelet inverse transform unit 77-3 performs three-dimensional wavelet inverse transform for the low-frequency volume data from the nonlinear anisotropic diffusion filter unit 73-3 and the high-frequency volume data from the high-frequency voxel control unit 75-3, and outputs single synthesis volume data. The synthesis volume data is supplied as low-frequency volume data to the nonlinear anisotropic diffusion filter unit 73-2 at level 2.

The nonlinear anisotropic diffusion filter unit 73-2 performs the same filter processing as that at level 3 for the low-frequency volume data from the three-dimensional wavelet inverse transform unit 77-3, and supplies the low-frequency volume data after filter processing to the wavelet inverse transform unit 77-2 at level 2. The high-frequency voxel control unit 75-2 at level 2 controls the voxel values of the seven types of high-frequency volume data from the three-dimensional wavelet transform unit 71-2 at level 2 in the same manner as that at level 3. The high-frequency voxel control unit 75-2 supplies the seven types of high-frequency volume data, in which the voxel values are controlled, to the wavelet inverse transform unit 77-2 at level 2. The wavelet inverse transform unit 77-2 performs three-dimensional wavelet inverse transform for the low-frequency volume data from the nonlinear anisotropic diffusion filter unit 73-2 and the seven types of high-frequency volume data from the high-frequency voxel control unit 75-2 by the same method as that at level 3, and outputs single synthesis volume data. The synthesis volume data is supplied as low-frequency volume data to the nonlinear anisotropic diffusion filter unit 73-1 at level 1.

The low-frequency volume data supplied to the nonlinear anisotropic diffusion filter unit 73-1 is subjected to the same filter processing as that at level 2 and level 3. The resultant data is supplied to the wavelet inverse transform unit 77-1 at level 1. The high-frequency voxel control unit 75-1 at level 1 performs the same voxel value control as that at level 2 and level 3 for the seven types of high-frequency volume data output from the three-dimensional wavelet transform unit 71-1 at level 1. The resultant data are then supplied to the wavelet inverse transform unit 77-1 at level 1. The wavelet inverse transform unit 77-1 performs three-dimensional wavelet inverse transform for the low-frequency volume data and the seven types of high-frequency volume data in the same manner as that at level 2 and level 3, and outputs single synthesis volume data. The number of samples per coordinate axis of the output synthesis volume data is equal to the number of samples per coordinate axis of the volume data input to the speckle/noise reduction processing unit 7.

The synthesis volume data generated by the three-dimensional wavelet inverse transform unit 77-1 at level 1 is supplied to the three-dimensional image processing unit 8. The three-dimensional image processing unit 8 generates the data of an ultrasonic image (two-dimensional image) by performing three-dimensional image processing for the synthesis volume data. On the generated ultrasonic image, the isotropic structures are reduced, and the anisotropic structures are enhanced. That is, speckle and noise on the ultrasonic image are reduced. The display unit 9 displays the generated ultrasonic image.

According to the above arrangement, the following effects can be obtained.

As described above, the ultrasonic diagnosis apparatus according to this embodiment calculates edge information for each voxel of input volume data based on a three-dimensional structure tensor. The ultrasonic diagnosis apparatus calculates a three-dimensional filter (diffusion equation (1)) for each voxel based on the edge information. The three-dimensional filter has a filter intensity and filter direction corresponding to the three-dimensional directivity of each voxel. The ultrasonic diagnosis apparatus smoothes each structure in the input volume data along the edge direction of the structure (all directions within a contact surface of the voxel to be processed) and sharpens each structure in a direction perpendicular to the edge direction (the normal direction of the contact surface of the voxel to be processed) by applying the calculated three-dimensional filter to the input volume data. If, for example, a structure has a tabular shape, this apparatus smoothes the structure along its plane (the $\omega_2\omega_3$ plane in FIG. 5), and sharpens the structure along the normal direction of the plane (the $\omega_1$ direction in FIG. 5). In this manner, the ultrasonic diagnosis apparatus can apply the optimal three-dimensional filter to volume data in accordance with the shape of each structure.

More specifically, the ultrasonic diagnosis apparatus according to this embodiment analyses volume data into low-frequency volume data and high-frequency volume data by executing three-dimensional multiresolution analysis by applying a low-pass filter and a high-pass filter to the volume data along each coordinate axis. The ultrasonic diagnosis apparatus then applies a nonlinear anisotropic diffusion filter to the low-frequency volume data. Applying the nonlinear anisotropic diffusion filter will generate low-frequency volume data in which each edge component contained in it is enhanced and each non-edge component such as speckle or noise is reduced. When applying the nonlinear anisotropic diffusion filter, it is necessary to discriminate the structure pattern of each structure in accordance with the magnitude relationship between the eigenvalues of the three-dimensional structure tensor. The ultrasonic diagnosis apparatus according to this embodiment discriminates a three-dimensional structure pattern by using only the maximum and minimum values of the three eigenvalues. This decreases the amount of processing to be performed and increases the processing speed as compared with a case in which three eigenvalues are used. This improvement is also desirable from the viewpoint of the real-time performance of image display which is a merit of the ultrasonic diagnosis apparatus.

In addition, the ultrasonic diagnosis apparatus according to this embodiment enhances each edge component in high-frequency volume data and reduces each non-edge component by using the edge information obtained by a nonlinear anisotropic diffusion filter. That is, when enhancing each edge component corresponding to high-frequency volume data, this apparatus uses edge information obtained in advance. This eliminates the necessity to newly specify the position information or the like of an edge component. This also increases the processing speed as compared with the prior art.

This apparatus performs multiresolution synthesis of edge-enhanced low-frequency volume data and high-frequency volume data to generate output volume data in which each non-edge component is reduced and each edge component is enhanced. This output volume data is generated by using three-dimensional multiresolution analysis/synthesis and a three-dimensional expansion filter. Therefore, speckle/noise reduction processing according to this embodiment is not influenced by the coordinate axis directions as compared with a case in which a two-dimensional filter is applied to volume data as in the prior art, and it is possible to uniformly reduce speckle and noise without any three-dimensional offset as compared with the prior art.

As described above, the ultrasonic diagnosis apparatus, the image processing apparatus, the control method for the ultrasonic diagnosis apparatus, and the image processing method according to this embodiment improve the reduction accuracy of speckle and noise contained in volume data and increase the reduction processing speed.

(First Modification)

An ultrasonic diagnosis apparatus, an image processing apparatus 12, a control method for the ultrasonic diagnosis apparatus, and an image processing method according to the first modification of this embodiment will be described below. Note that the same reference numerals as in this embodiment denote constituent elements having almost the same functions and arrangements, and a repetitive description will be made only when required.

The ultrasonic diagnosis apparatus according to the first modification executes speckle/noise reduction processing after performing three-dimensional image processing for volume data. FIG. 9 is a block diagram showing the arrangement of the ultrasonic diagnosis apparatus according to the first modification. The B-mode volume data generating unit 4 supplies generated B-mode volume data to the three-dimensional image processing unit 8. The Doppler volume data generating unit 6 supplies generated Doppler volume data to the three-dimensional image processing unit 8. The three-dimensional image processing unit 8 performs three-dimensional image processing for the supplied volume data such as B-mode volume data and Doppler volume data to generate the data of a cross-sectional image with thickness. The generated data of the cross-sectional image with thickness is supplied to the speckle/noise reduction processing unit 7.

The speckle/noise reduction processing unit 7 reduces speckle and noise by executing speckle/noise reduction processing unique to this embodiment for the supplied cross-sectional image with thickness. If each cross-section of the cross-sectional image with thickness is defined as an xy plane and the thickness direction is the z-axis direction, the processing method to be used for the image is the same as the three-dimensional image processing method according to this embodiment. In the first modification, however, the number of samples in the z-axis direction is considerably smaller than that in the x- and y-axis directions. If the processing result is displayed as a plane, the number of samples in the z-axis direction after processing is 1. When a plane is to be formed after another type of processing such as MIP is performed after the reduction processing, the image after the reduction processing is still the cross-sectional image with thickness, and the number of samples in the z-axis direction is plural. The data of the thick cross-sectional image in which speckle and noise are reduced is supplied to the three-dimensional image processing unit 8 again.

The three-dimensional image processing unit 8 generates the data of a two-dimensional ultrasonic image by performing three-dimensional image processing for the data of the cross-sectional image with thickness in which speckle and noise are reduced. The generated data of the ultrasonic image is supplied to the display unit 9.

The display unit 9 displays the ultrasonic image supplied from the three-dimensional image processing unit 8.

In this manner, the first modification can provide an ultrasonic diagnosis apparatus, an image processing apparatus, a control method for the ultrasonic diagnosis apparatus, and an image processing method which improve the reduction accuracy of speckle and noise contained in volume data and increase the reduction processing speed.

(Second Modification)

The image processing apparatus 12 according to the above embodiment is incorporated in the ultrasonic diagnosis apparatus. However, this embodiment need not be limited to this. For example, the image processing apparatus 12 may be incorporated in an X-ray computed tomography apparatus, magnetic resonance imaging apparatus, or nuclear medicine diagnosis apparatus. In addition, the image processing apparatus 12 may be a workstation connected to an image diagnosis apparatus such as an ultrasonic diagnosis apparatus, X-ray computed diagnosis apparatus, magnetic resonance imaging apparatus, or nuclear medicine diagnosis apparatus via a network. That is, volume data to be processed according to this embodiment does not depend on the type of image diagnosis apparatus. The image processing apparatus 12 according to the second modification can execute the above speckle/noise reduction processing for the volume data generated by any type of image diagnosis apparatus including an ultrasonic diagnosis apparatus, X-ray computed diagnosis apparatus, magnetic resonance imaging apparatus, and nuclear medicine diagnosis apparatus.

The second modification can therefore provide an image processing apparatus and image processing method which improve reduction accuracy of speckle and noise contained in volume data and increase the reduction processing speed.

Additional advantages and modifications will readily occur to those skilled in the art. Therefore, the invention in its broader aspects is not limited to the specific details and representative embodiments shown and described herein. Accordingly, various modifications maybe made without departing from the spirit or scope of the general inventive concept as defined by the appended claims and their equivalents.

What is claimed is:

1. An ultrasonic diagnosis apparatus comprising:
an ultrasonic probe;
a transmission/reception circuit configured to transmit an ultrasonic wave to a subject via the ultrasonic probe and receive an echo signal corresponding to an ultrasonic wave reflected by the subject; and
processing circuit configured to
generate first volume data based on the received echo signal;
generate low-frequency volume data and high-frequency volume data on spatial frequencies based on the generated first volume data;
calculate three eigenvalues, identify three-dimensional structure patterns of three-dimensional structures indicating a degree of anisotropic structure components and isotropic structure components contained in the generated low-frequency volume data using the three eigenvalues, calculate edge information in accordance with the identified structure patterns using two eigenvalues of the three eigenvalues, and apply a nonlinear anisotropic diffusion filter having a filter characteristic corresponding to the calculated edge information to the low-frequency volume data;
perform edge enhancement processing for the high-frequency volume data using the generated edge information; and
generate second volume data with reduced speckle and reduced noise based on the low-frequency volume data to which the nonlinear anisotropic diffusion filter is applied and the high-frequency volume data for which edge enhancement processing is performed.

2. An ultrasonic diagnosis apparatus comprising:
an ultrasonic probe;
a transmission/reception circuit configured to transmit an ultrasonic wave to a subject via the ultrasonic probe, receive an ultrasonic wave reflected by the subject, and output an echo signal corresponding to the received ultrasonic wave; and
a processing circuit configured to
generate first volume data based on the echo signal;
generate second volume data by applying, to each voxel contained in the first volume data, three-dimensional filtering with a filtering characteristic derived from three-dimensional directivity of the voxel; and
generate data of a two-dimensional ultrasonic image based on the second volume data.

3. The apparatus according to claim 2, wherein the processing circuit calculates an intensity and direction of three-dimensional diffusion of the voxel based on a value of the voxel and values of a plurality of neighboring voxels located near the voxel, and determines the filtering characteristic in accordance with the calculated intensity and direction of three-dimensional diffusion.

4. The apparatus according to claim 2, wherein the processing circuit is further configured to
generate low-frequency volume data and high-frequency volume data on spatial frequencies based on the generated first volume data,
calculate three eigenvalues for classifying three-dimensional structure patterns of three-dimensional structures indicating a degree of anisotropic structure components and isotropic structure components contained in the generated low-frequency volume data using the three eigenvalues, calculate edge information in accordance with the identified structure patterns based on two eigenvalues of the three eigenvalues, and apply a nonlinear anisotropic diffusion filter having a filter characteristic corresponding to the calculated edge information to the low-frequency volume data;
perform edge enhancement processing for the high-frequency volume data based on the generated edge information; and
generate second volume data with reduced speckle and reduced noise based on the low-frequency volume data to which the nonlinear anisotropic diffusion filter is applied by the filter unit and the high-frequency volume data for which edge enhancement processing is performed.

5. The apparatus according to claim 4, wherein the processing circuit generates the low-frequency volume data and the high-frequency volume data by performing multiresolution analysis of the generated first volume data, and
generates the second volume data by performing multi-resolution synthesis of low-frequency volume data to which the nonlinear anisotropic diffusion filter is applied unit and high-frequency volume data for which edge enhancement processing is performed.

6. The apparatus according to claim 5, wherein the multi-resolution analysis/synthesis includes wavelet transform/inverse transform, a Laplacian pyramid method, and Gabor transform/inverse transform.

7. The apparatus according to claim 2, further comprising a display configured to display the ultrasonic image.

8. An ultrasonic diagnosis apparatus, comprising:
an ultrasonic probe;
a transmission/reception circuit configured to transmit an ultrasonic wave to a subject via the ultrasonic probe, receive an ultrasonic wave reflected by the subject, and output an echo signal corresponding to the received ultrasonic wave; and
processing circuit configured to
generate first volume data based on the echo signal;
generate second volume data from the first volume data by identifying a three-dimensional isotropic structure component and a three dimensional anisotropic structure component, reducing the three-dimensional isotropic structure component, and enhancing the three-dimensional anisotropic structure component, the three-dimensional isotropic structure component and the three-dimensional anisotropic structure component being contained in the first volume data; and
generate data of a two-dimensional ultrasonic image by performing three-dimensional image processing for the second volume data.

9. The apparatus according to claim 8, wherein the processing circuit is further configured to
perform multiresolution analysis of the first volume data to generate first low-frequency volume data and first high-frequency volume data,
calculate an eigenvalue and eigenvector of a three-dimensional structure tensor based on the first low-frequency volume data,
apply a filter to the first low-frequency volume data along a direction corresponding to the eigenvector to generate second low-frequency volume data, the filter having an intensity of diffusion corresponding to the eigenvalue,
control a value of a voxel contained in the first high-frequency volume data based on the eigenvalue to generate second high-frequency volume data, and
perform multiresolution synthesis of the second low-frequency volume data and the second high-frequency volume data to generate the second volume data.

10. The apparatus according to claim 9, wherein the processing circuit calculates three eigenvalues of the three-dimensional structure tensor, and
calculates edge information associated with a magnitude of an edge component contained in the first low-frequency volume data based on a maximum eigenvalue and minimum eigenvalue of the three eigenvalues, and applies a nonlinear anisotropic diffusion filter having the intensity of diffusion corresponding to the magnitude of the edge information to the first low-frequency volume data.

11. The apparatus according to claim 9, wherein the multiresolution analysis/synthesis includes wavelet transform/inverse transform, a Laplacian pyramid method, and Gabor transform/inverse transform.

12. The apparatus according to claim 8, further comprising a display configured to display the ultrasonic image.

13. An image processing apparatus, comprising:
a memory configured to store first volume data associated with a subject; and
a processing circuit configured to
generate second volume data by applying, to each voxel contained in the first volume data, three-dimensional filtering with a filtering characteristic derived from three-dimensional directivity of the voxel; and
generate data of a two-dimensional ultrasonic image based on the second volume data.

14. The apparatus according to claim 13, wherein the processing circuit calculates an intensity and direction of three-dimensional diffusion of the voxel based on a value of the voxel and values of a plurality of neighboring voxels located near the voxel, and determines the filtering characteristic in accordance with the calculated intensity and direction of three-dimensional diffusion.

15. The apparatus according to claim 13, wherein the processing circuit is further configured to
generate low frequency volume data and high-frequency volume data on spatial frequencies based on the generated first volume data,
calculate three eigenvalues for classifying three-dimensional structure patterns of three-dimensional structures indicating a degree of anisotropic structure components and isotropic structure components contained in the generated low-frequency volume data using the three eigenvalues, calculate edge information in accordance with the identified structure patterns based on two eigenvalues of the three eigenvalues, and apply a nonlinear anisotropic diffusion filter having a filter characteristic corresponding to the calculated edge information to the low-frequency volume data;
perform edge enhancement processing for the high-frequency volume data based on the generated edge information; and
generate second volume data with reduced speckle and reduced noise based on the low-frequency volume data to which the nonlinear anisotropic diffusion filter is applied and the high-frequency volume data for which edge enhancement processing is performed.

16. The apparatus according to claim 15, wherein the processing circuit generates the low-frequency volume data and the high-frequency volume data by performing multiresolution analysis of the generated first volume data, and
generates the second volume data by performing multiresolution synthesis of low-frequency volume data to which the nonlinear anisotropic diffusion filter is applied and high-frequency volume data for which edge enhancement processing is performed.

17. The apparatus according to claim 16, wherein the multiresolution analysis/synthesis includes wavelet transform/inverse transform, a Laplacian pyramid method, and Gabor transform/inverse transform.

18. The apparatus according to claim 13, further comprising a display configured to display the ultrasonic image.

19. An image processing apparatus, comprising:
a memory configured to store first volume data associated with a subject;
a processing circuit configured to
generate second volume data from the first volume data by identifying a three-dimensional isotropic structure component and a three dimensional anisotropic structure component, reducing the three-dimensional isotropic structure component, and enhancing the three-dimensional anisotropic structure component, the three-dimensional isotropic structure component and the three-dimensional anisotropic structure component being contained in the first volume data; and
generate data of a two-dimensional image by performing three-dimensional image processing for the second volume data.

20. The apparatus according to claim 19, wherein the processing circuit is further configured to
perform multiresolution analysis of the first volume data to generate first low-frequency volume data and first high-frequency volume data, calculate an eigenvalue and eigenvector of a three-dimensional structure tensor based on the first low-frequency volume data, apply a filter to the first low-frequency volume data along a direction corresponding to the eigenvector to generate second low-frequency volume data, the filter having an intensity of diffusion corresponding to the eigenvalue, control a value of a voxel contained in the first high-frequency volume data based on the eigenvalue to generate second high-frequency volume data, and perform multiresolution synthesis of the second low-frequency volume data and the second high-frequency volume data to generate the second volume data.

21. The apparatus according to claim 20, wherein the processing circuit calculates three eigenvalues of the three-dimensional structure tensor, and calculates edge information associated with a magnitude of an edge component contained in the first low-frequency volume data based on a maximum eigenvalue and minimum eigenvalue of the three eigenvalues, and applies a nonlinear anisotropic diffusion filter having the intensity of diffusion corresponding to the magnitude of the edge information to the first low-frequency volume data.

22. The apparatus according to claim 20, wherein the multiresolution analysis/synthesis includes wavelet transform/inverse transform, a Laplacian pyramid method, and Gabor transform/inverse transform.

23. The apparatus according to claim 19, further comprising a display configured to display the two-dimensional image.

24. A control method for an ultrasonic diagnosis apparatus, the ultrasonic diagnosis apparatus which comprises an ultrasonic probe, a transmission/reception circuit configured to transmit and receive ultrasonic waves via the ultrasonic probe, and a processing circuit, the processing circuit being configured to:

cause the transmission/reception circuit to transmit an ultrasonic wave to a subject via the ultrasonic probe, receive an ultrasonic wave reflected by the subject via the ultrasonic probe, and output an echo signal corresponding to the received ultrasonic wave;

generate first volume data based on the received echo signal;

generate low-frequency volume data and high-frequency volume data on spatial frequencies based on the generated first volume data;

calculate three eigenvalues, identify three-dimensional structure patterns of three-dimensional structures indicating a degree of anisotropic structure components and isotropic structure components contained in the generated low-frequency volume data using the three eigenvalues, calculate edge information in accordance with the identified structure patterns based on two eigenvalues of the three eigenvalues, and apply a nonlinear anisotropic diffusion filter having a filter characteristic corresponding to the calculated edge information to the low-frequency volume data;

perform edge enhancement processing for the high-frequency volume data based on the generated edge information; and generate second volume data with reduced speckle and reduced noise based on the low-frequency volume data to which the nonlinear anisotropic diffusion filter is applied and the high-frequency volume data for which edge enhancement processing is performed.

25. A control method for an ultrasonic diagnosis apparatus, the ultrasonic diagnosis apparatus comprises an ultrasonic probe, a transmission/reception circuit configured to transmit and receive ultrasonic waves via the ultrasonic probe, and a processing circuit, the processing circuit configured to:

cause the transmission/reception circuit to transmit an ultrasonic wave to a subject via the ultrasonic probe, receive an ultrasonic wave reflected by the subject via the ultrasonic probe, and output an echo signal corresponding to the received ultrasonic wave;

generate first volume data based on the output echo signal;

generate second volume data by applying, to each voxel contained in the first volume data, three-dimensional filtering with a filtering characteristic derived from three-dimensional directivity of the voxel; and generate data of a two-dimensional ultrasonic image based on the second volume data.

26. The method according to claim 25, wherein the processing circuit is further configured to calculate an intensity and direction of three-dimensional diffusion of the voxel based on a value of the voxel and values of a plurality of neighboring voxels located near the voxel, and determine the filtering characteristic in accordance with the calculated intensity and direction of three-dimensional diffusion.

27. The method according to claim 25, wherein the processing circuit is further configured to generate low-frequency volume data and high-frequency volume data on spatial frequencies based on the generated first volume data, calculate three eigenvalues for classifying three-dimensional structure patterns of three-dimensional structures contained in the generated low-frequency volume data, calculate edge information based on two eigenvalues of the three eigenvalues, apply a nonlinear anisotropic diffusion filter having a filter characteristic corresponding to the calculated edge information to the low-frequency volume data, perform edge enhancement processing for the high-frequency volume data based on the generated edge information, and generate second volume data with reduced speckle and reduced noise based on the low-frequency volume data to which the nonlinear anisotropic diffusion filter is applied and the high-frequency volume data for which edge enhancement processing is performed.

28. An image processing method comprising:

generating low-frequency volume data and high-frequency volume data on spatial frequencies based on first volume data associated with a subject;

calculating three eigenvalues and identifying three-dimensional structure patterns of three-dimensional structures indicating a degree of anisotropic structure components and isotropic structure components contained in the generated low-frequency volume data using the three eigenvalues;

calculating edge information in accordance with the identified structure pattern based on two eigenvalues of the three eigenvalues;

applying a nonlinear anisotropic diffusion filter having a filter characteristic corresponding to the calculated edge information to the low-frequency volume data;

performing edge enhancement processing for the high-frequency volume data based on the generated edge information; and generating second volume data with reduced speckle and reduced noise based on the low-frequency volume data to which the nonlinear anisotropic diffusion filter is applied and the high-frequency volume data for which edge enhancement processing is performed.

29. An image processing method comprising:

generating second volume data by applying, to each voxel contained in generated first volume data associated with a subject, three-dimensional filtering with a filtering characteristic derived from three-dimensional directivity of the voxel; and generating data of a two-dimensional image based on the second volume data.

30. The method according to the claim 29, wherein generating second volume data calculates an intensity and direction of three-dimensional diffusion of the voxel based on a value of the voxel and values of a plurality of neighboring voxels located near the voxel, and determines the filtering characteristic in accordance with the calculated intensity and direction of three-dimensional diffusion.

31. The method according to claim 29, wherein generating second volume data generates low-frequency volume data and high-frequency volume data on spatial frequencies based on the generated first volume data, calculates three eigenvalues for classifying three-dimensional structure patterns of three-dimensional structures contained in the generated low-frequency volume data, calculates edge information based on two eigenvalues of the three eigenvalues, applies a nonlinear anisotropic diffusion filter having a filter characteristic corresponding to the calculated edge information to the low-frequency volume data; performs edge enhancement processing for the high-frequency volume data based on the generated edge information; and generates second volume data with reduced speckle and reduced noise based on the low-frequency volume data to which the nonlinear anisotropic diffusion filter is applied and the high-frequency volume data for which edge enhancement processing is performed.

32. The method of claim 28, wherein the step of identifying the three-dimensional structure patterns comprises:

classifying the three-dimensional structures into three-dimensional isotropic structure components and three-dimensional anisotropic structure components using the calculated three eigenvalues.

* * * * *